(12) United States Patent
Sekido (10) Patent No.: US 10,290,393 B2
(45) Date of Patent: May 14, 2019

(54) MOUNTING CABLE AND CABLE ASSEMBLY

(71) Applicant: OLYMPUS CORPORATION, Tokyo (JP)

(72) Inventor: Takanori Sekido, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/790,132

(22) Filed: Jul. 2, 2015

(65) Prior Publication Data

US 2016/0005513 A1    Jan. 7, 2016

(30) Foreign Application Priority Data

Jul. 2, 2014    (JP) .................................. 2014-137139

(51) Int. Cl.
*H01B 11/18*    (2006.01)
*H01B 7/02*    (2006.01)
(Continued)

(52) U.S. Cl.
CPC ....... *H01B 7/0216* (2013.01); *A61B 1/00124* (2013.01); *H01R 9/05* (2013.01); *H01R 13/025* (2013.01); *H01R 24/50* (2013.01); *H01R 2201/12* (2013.01); *H05K 1/0215* (2013.01); *H05K 1/0284* (2013.01); *H05K 3/103* (2013.01); *H05K 2201/09781* (2013.01); *H05K 2201/10189* (2013.01)

(58) Field of Classification Search
CPC ........ H01B 11/18; H01B 7/0216; H01B 7/40; H01R 9/05

USPC ....................................................... 174/75 C
See application file for complete search history.

(56) References Cited

U.S. PATENT DOCUMENTS 4,321,930 A * 3/1982 Jobsis .................. A61B 5/0059
                                                    600/344
7,364,461 B1 * 4/2008 Back ..................... H01R 9/0515
                                                    439/329

(Continued)

FOREIGN PATENT DOCUMENTS

JP    2008-112699 A    5/2008
JP    2010-108635 A    5/2010
(Continued)

OTHER PUBLICATIONS

Decision to Grant a Patent dated Jan. 9, 2018 in Japanese Patent Application No. 2014-137139.

*Primary Examiner* — Stanley Tso
(74) *Attorney, Agent, or Firm* — Scully, Scott, Murphy & Presser, P.C.

(57) ABSTRACT

A mounting cable includes: a metal cable that includes a core wire formed of a conductive material and a jacket formed of an insulator and covering the core wire; a cable fixing portion that fixes an end portion of the metal cable, and has an end face which is perpendicular to an axial direction of the metal cable and on which a cross section of an end portion of the core wire is exposed; an external connection electrode formed on at least one surface of the cable fixing portion, the at least one surface being in parallel with the axial direction of the metal cable; and a wire pattern that extends from an area on the core wire exposed on the end face to the external connection electrode.

12 Claims, 11 Drawing Sheets

(51) Int. Cl.
*A61B 1/00* (2006.01)
*H01R 9/05* (2006.01)
*H01R 13/02* (2006.01)
*H01R 24/50* (2011.01)
*H05K 1/02* (2006.01)
*H05K 3/10* (2006.01)

(56) References Cited

U.S. PATENT DOCUMENTS

| | | | | |
|---|---|---|---|---|
| 8,298,008 | B2* | 10/2012 | Negishi | A61B 1/042 |
| | | | | 439/579 |
| 8,513,536 | B2* | 8/2013 | Negishi | H01R 9/0515 |
| | | | | 174/260 |
| 9,186,042 | B2* | 11/2015 | Saito | A61B 1/00105 |
| 2008/0026612 | A1* | 1/2008 | Malstrom | H01R 13/65807 |
| | | | | 439/79 |
| 2008/0038962 | A1* | 2/2008 | Neumetzler | H01R 13/6633 |
| | | | | 439/638 |
| 2009/0029589 | A1* | 1/2009 | Conner | H01R 24/50 |
| | | | | 439/579 |
| 2009/0035990 | A1* | 2/2009 | McCarthy | H01R 9/0518 |
| | | | | 439/585 |
| 2011/0042140 | A1* | 2/2011 | Nakamura | A61B 1/00114 |
| | | | | 174/84 R |
| 2015/0185430 | A1* | 7/2015 | Jin | G02B 6/4448 |
| | | | | 385/135 |

FOREIGN PATENT DOCUMENTS

| | | |
|---|---|---|
| JP | 2011-071036 A | 4/2011 |
| JP | 2012-014934 A | 1/2012 |

* cited by examiner

MOUNTING CABLE AND CABLE ASSEMBLY

CROSS REFERENCES TO RELATED APPLICATIONS

This application is based upon and claims the benefit of priority from Japanese Patent Application No. 2014-137139, filed on Jul. 2, 2014, the entire contents of which are incorporated herein by reference.

BACKGROUND

1. Technical Field

The disclosure relates to a mounting cable and a cable assembly.

2. Related Art

Medical and industrial endoscopes have been widely used in recent years. Some medical endoscopes are provided with, for example, an imaging apparatus that includes a CCD or other imaging element built therein at a distal end of an inserting portion to be introduced into the body. Deeply inserting this inserting portion into the body allows a lesion site to be observed. When a treatment tool is used in combination with the endoscope as necessary, an examination or treatment may be performed inside the body.

To display an image on a monitor in such a type of endoscope, image information captured by the imaging element is converted to a corresponding electric signal and the resultant electric signal is transmitted to a signal processor via a signal line, so that the signal processor can perform signal processing. The imaging element in the endoscope and the signal processor are connected to each other through a cable assembly that includes a plurality of cables bound together for, for example, transmitting image signals and clock signals and supplying the imaging element with drive power.

As a technique for collectively connecting, for example, a cable assembly to a substrate, a known technique is directed to connection of a coaxial cable array including a plurality of coaxial cables fixed with a cable fixing portion formed of a resin molding to a substrate (see, for example, Japanese Patent Application Laid-open No. 2010-108635).

SUMMARY

In some embodiments, a mounting cable includes: a metal cable that includes a core wire formed of a conductive material and a jacket formed of an insulator and covering the core wire; a cable fixing portion that fixes an end portion of the metal cable, and has an end face which is perpendicular to an axial direction of the metal cable and on which a cross section of an end portion of the core wire is exposed; an external connection electrode formed on at least one surface of the cable fixing portion, the at least one surface being in parallel with the axial direction of the metal cable; and a wire pattern that extends from an area on the core wire exposed on the end face to the external connection electrode.

In some embodiments, a cable assembly includes: a plurality of cables, at least one of which is a metal cable that includes a core wire formed of a conductive material and a jacket formed of an insulator and covering the core wire; a cable fixing portion that fixes distal end portions of the plurality of cables, and has an end face which is perpendicular to an axial direction of the plurality of cables and on which cross sections of end portions of core wires of the plurality of cables are exposed; at least one external connection electrode formed on at least one surface of the cable fixing portion, the at least one surface being in parallel with the axial direction of the plurality of cables; and a wire pattern that extends from an area on the core wire of the metal cable exposed on the end face to the at least one external connection electrode.

The above and other features, advantages and technical and industrial significance of this invention will be better understood by reading the following detailed description of presently preferred embodiments of the invention, when considered in connection with the accompanying drawings.

DETAILED DESCRIPTION

Modes for carrying out the present invention (hereinafter referred to as "embodiment(s)") will be described below with reference to the accompanying drawings. It should be noted that the embodiment is not intended to limit the present invention. The same reference signs are used to designate the same elements throughout the drawings. The drawings are schematic and are not scaled to exact sizes, so that care should be used to note that, for example, a thickness to a width in one member and a ratio of one member to another may be different from they are in actual mechanism. The drawings further contain portions of varying dimensional relations and ratios among different drawings.

First Embodiment

Figure 1:
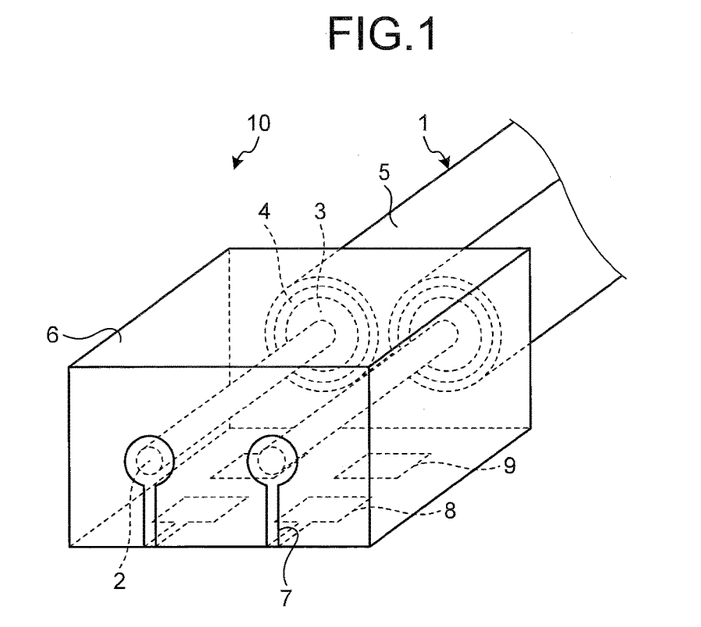
FIG. 1 is a perspective view of a cable assembly according to a first embodiment of the present invention.
Figure 2:
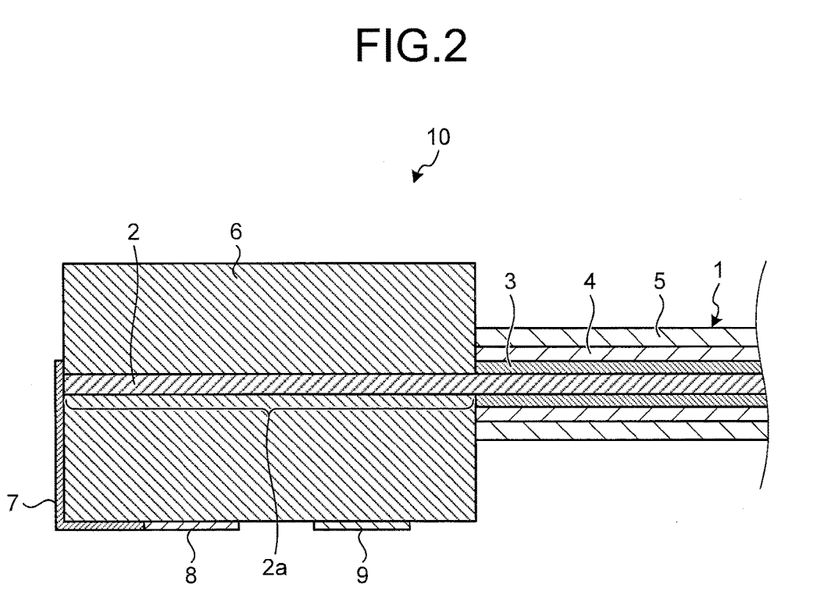
FIG. 2 is a sectional view of the cable assembly illustrated in FIG. 1.

Reference will be made to a cable connection structure according to a first embodiment. FIG. 1 is a perspective view of a cable assembly according to the first embodiment of the present invention. FIG. 2 is a sectional view of the cable assembly illustrated in FIG. 1.

As illustrated in FIGS. 1 and 2, this cable assembly 10 according to the first embodiment includes two cables 1 as metal cables and a cable fixing portion 6 that fixes in place the cables 1.

Each of the cables 1 is a coaxial cable that includes a core wire 2, an inner insulator 3, a shield 4, and a jacket 5. Specifically, the core wire 2 is formed of a conductive material. The inner insulator 3 covers an outer periphery of the core wire 2. The shield 4 covers an outer periphery of the inner insulator 3. The jacket 5 formed of an insulator covers an outer periphery of the shield 4. The inner insulator 3, the shield 4, and the jacket 5 peel off at a distal end of the cable 1 to thereby form a core wire exposed portion 2a over which the core wire 2 is exposed. The cable fixing portion 6 directly covers the core wire exposed portion 2a. The direct fixing of the core wire 2 by the cable fixing portion 6 prevents the core wire 2 from being moved in an axial direction of the core wire 2 when stress is applied to the cable 1. It is noted that, provided that the core wire exposed portion 2a over which the core wire 2 is exposed is disposed inside the cable fixing portion 6, the inner insulator 3, the shield 4, the jacket 5, and the like may be exposed in a stepwise fashion at the distal end of the cable 1 inside the cable fixing portion 6.

Preferably, the cable fixing portion 6 is formed of a thermosetting resin having an insulation property; however, a photosetting resin such as an ultraviolet curable resin or a naturally curable resin may be used. An epoxy resin is preferably used as the thermosetting resin used for the cable fixing portion 6 in view of adhesion.

The cable fixing portion 6 is a rectangular parallelepiped. Thus, a cross section of an end portion of the core wire 2 is exposed on an end face of the cable fixing portion 6 perpendicular to an axial direction of the cable 1. The cable fixing portion 6 has a bottom surface that serves as a substrate connecting surface. An external connection electrode 8 and a dummy electrode 9 are disposed on the bottom surface of the cable fixing portion 6. A wire pattern 7 is formed to extend from the core wire 2 exposed on the end face to the external connection electrode 8.

Figure 3:
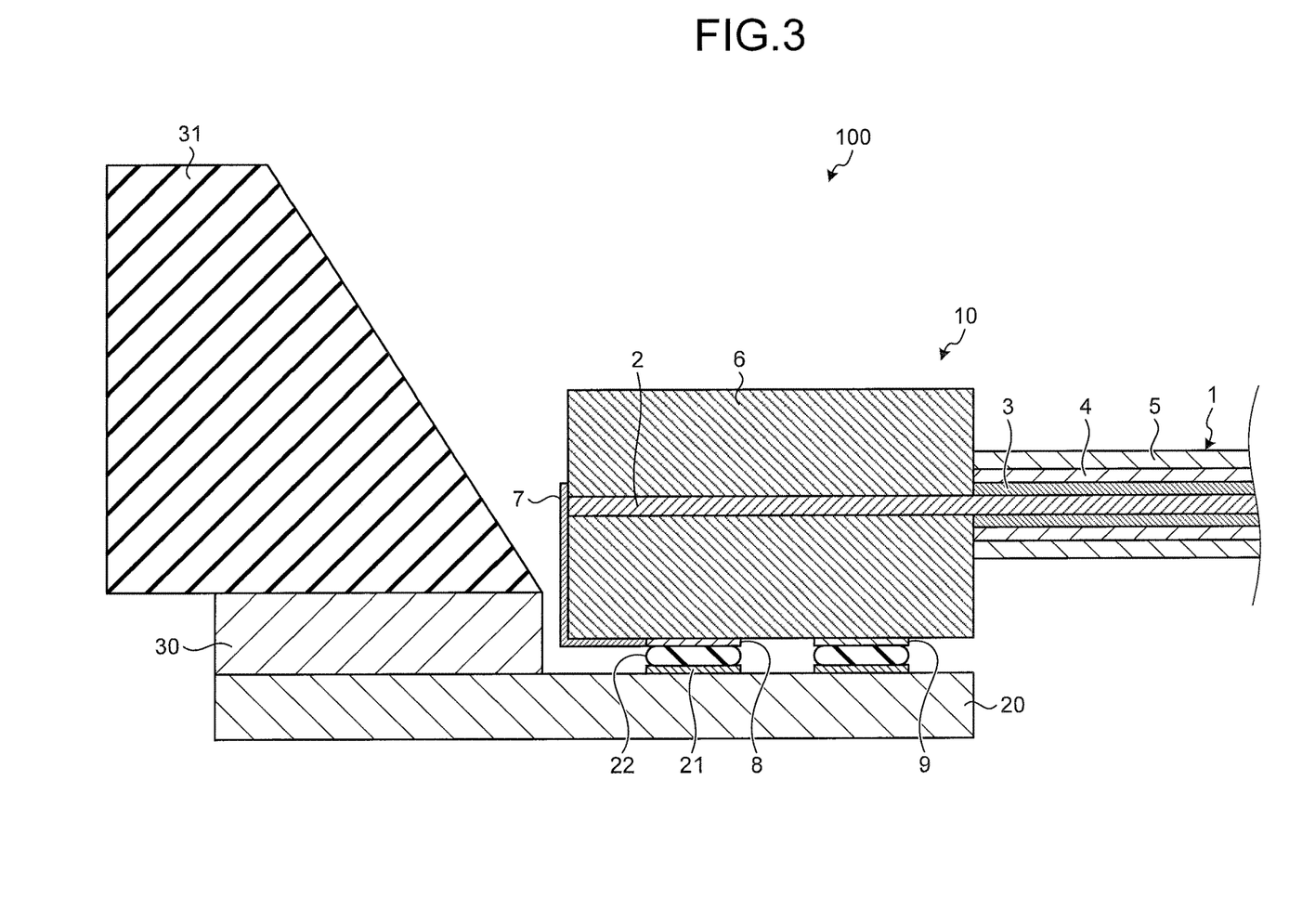
FIG. 3 is a sectional view of a cable connection structure in which the cable assembly illustrated in FIG. 1 is connected to a substrate.

As illustrated in FIG. 3, for example, the cable assembly 10 is connected to a substrate by the external connection electrode 8 and the dummy electrode 9. FIG. 3 is a sectional view of the cable connection structure in which the cable assembly illustrated in FIG. 1 is connected to a substrate. A cable connection structure 100 illustrated in FIG. 3 is used for an imaging module. The cable connection structure 100 includes the cable assembly 10, a substrate 20, an imaging element 30, and a prism 31.

The imaging element 30 is bonded to the prism 31. Having received light incident upon the prism 31 from an imaging optical system not illustrated, the imaging element 30 performs photo-electric conversion to thereby generate an electric signal. Meanwhile, the imaging element 30 is electrically connected to the substrate 20, so that the electric signal generated by the imaging element 30 is transmitted to the cable 1 via the substrate 20.

An electrode 21 and a circuit pattern (not illustrated) are formed on the substrate 20. The electrode 21 is connected to the external connection electrode 8 or the dummy electrode 9 by a conductive material 22 such as a solder.

In the cable assembly 10 according to the first embodiment, the cables 1 can be connected so as to have their axes extending in parallel with the substrate 20 without the need to be folded. The cable assembly 10 in the first embodiment thus requires no space for accommodating a cable 1 folding margin on the substrate 20. In addition, having no need to fold the core wire 2 prevents the core wire 2 from being open-circuited. It is noted that an external connection electrode may be additionally formed on a side surface portion of the cable fixing portion 6, for example, a surface of the cable fixing portion 6 opposed to a mounting surface of the external connection electrode 8 (specifically, an upper surface of the cable fixing portion 6) to thereby mount an electronic component. This arrangement reduces a portion on the substrate 20 on which electronic components are to be mounted, so that the cable connection structure 100 can be built more compactly.

Figure 4:
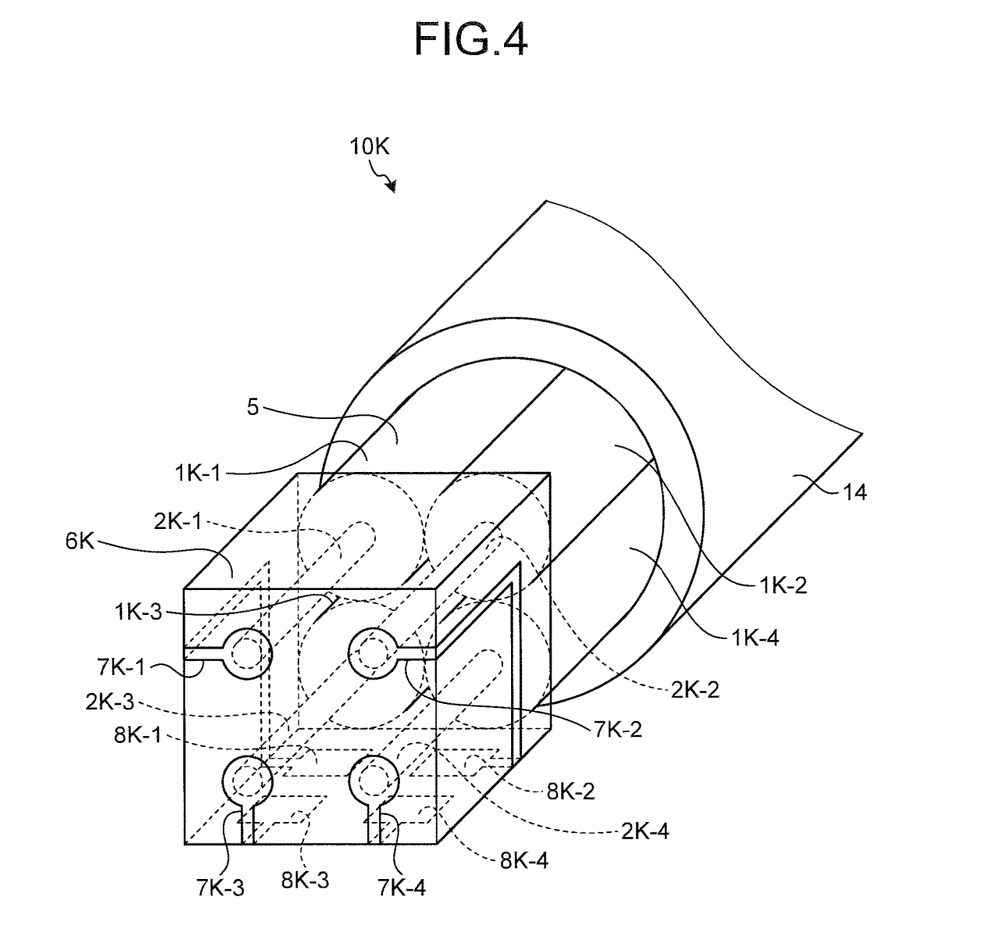
FIG. 4 is a perspective view of a cable assembly according to a first modification of the first embodiment of the present invention.

The cable assembly 10 has been described for a configuration including two cables 1. The cable assembly 10 may nonetheless include any number of cables 1. For example, the cable assembly 10 may include four cables as illustrated in FIG. 4. FIG. 4 is a perspective view of a cable assembly according to a first modification of the first embodiment of the present invention. In this cable assembly 10K in the first modification of the first embodiment of the present invention, four cables 1K (1K-1, 1K-2, 1K-3, and 1K-4) are disposed three-dimensionally. Specifically, two cables are disposed on another two cables each to form two upper and lower rows (the cables 1K-1 and 1K-2 disposed above the cables 1K-3 and 1K-4, respectively) and an outer jacket 14 covers the four cables 1K up to their proximal end sides. Each of the cables 1K is a metal cable that includes a jacket 5 formed of an insulator and covering an outer periphery of a core wire 2K (2K-1, 2K-2, 2K-3, and 2K-4). The outer jacket 14 peels off at a distal end portion and a cable fixing portion 6K fixes therein exposed core wires 2K.

Four external connection electrodes 8K (8K-1, 8K-2, 8K-3, and 8K-4), which are as many as the cables 1K, are disposed on a bottom surface of the cable fixing portion 6K. Wire patterns 7K (7K-1, 7K-2, 7K-3, and 7K-4) are formed from the core wires 2K exposed on an end face to the external connection electrodes 8K.

The arrangements in which the cables 1K are disposed three-dimensionally and the external connection electrodes 8K associated with the respective cables 1K are formed on the bottom surface that assumes one plane extending in parallel with the axial direction of the cables 1K, as in the cable assembly 10K according to the first modification of the first embodiment of the present invention, enable connection of the cable assembly 10K in a smaller connection area than in the arrangement in which the cables 1K are planarly disposed, specifically, four cables are disposed in parallel with each other in a single row. In addition, relative dispositions (layout) of the external connection electrodes 8K formed on the bottom surface preferably correspond to relative dispositions (layout) of ends of the core wires 2K of the cables 1K in an end face perpendicular to the axial direction of the cable assembly 10K. For example, the external connection electrode 8K-2 disposed at the upper right position as viewed from the upper surface side to the bottom surface side is electrically connected by the wire pattern 7K-2 to the core wire 2K-2 disposed at the upper right position as viewed from the end face side on which the core wires 2K are exposed. Matching the relative dispositions of the external connection electrodes 8K with those of the ends of the core wires 2K thus enables cable connections occupying a smaller connection area.

Disposing a plurality of cables three-dimensionally and forming a plurality of external connection electrodes, each of which is associated with a corresponding cable, on a single plane that extends in parallel with the axial direction of the cables of the cable fixing portion allows the area required for making connections to be reduced regardless of the number of cables involved. The first modification allows the connection area required for connecting the cable assembly that is composed of four cables, two each of which are disposed on another two cables each to form two sets of upper and lower rows, in the case where the cable assembly is connected to the substrate using the external connection electrodes, to be identical to the connection area required by the cable assembly that is composed of two cables disposed in a single row. The first modification also allows a cable assembly composed of two cables, one of which is disposed on another to form a set of upper and lower rows, to be connected to a connection area that is identical to that required by a cable assembly composed of one cable disposed in a single row.

Figure 5:
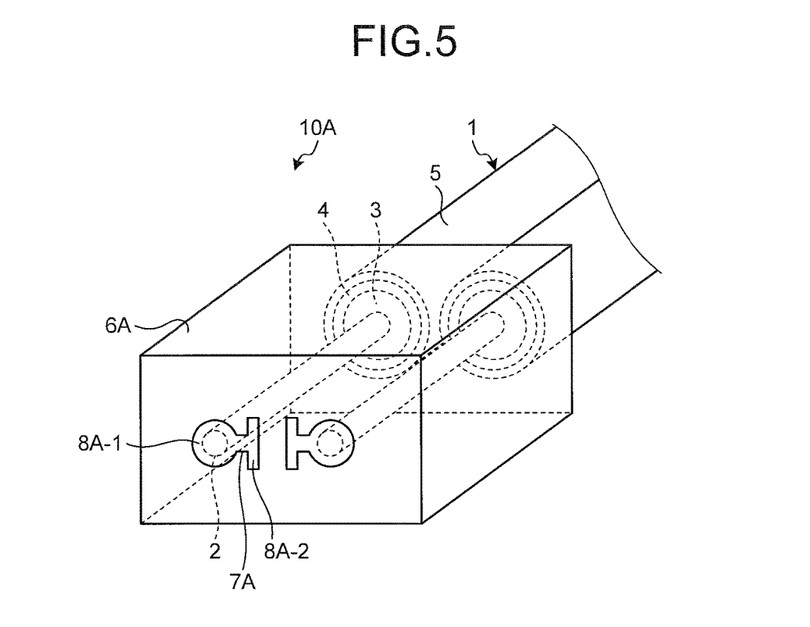
FIG. 5 is a perspective view of a cable assembly according to a second modification of the first embodiment of the present invention.
Figure 6:
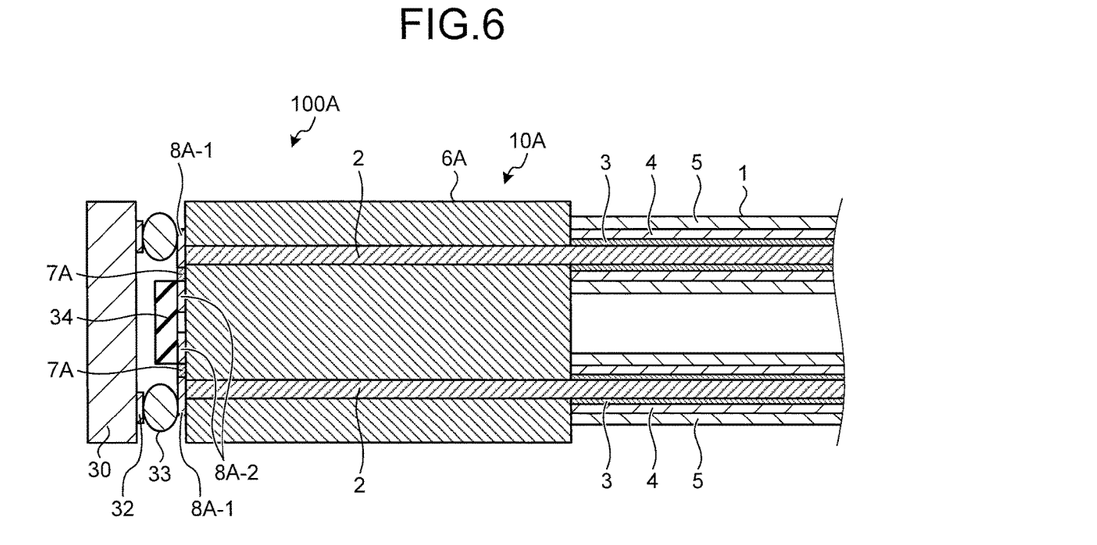
FIG. 6 is a sectional view of a cable connection structure in which an imaging element is connected to the cable assembly illustrated in FIG. 5.

The external connection electrode may still be formed on the end face of the cable fixing portion 6 on which the core wire 2 is exposed. FIG. 5 is a perspective view of a cable assembly according to a second modification of the first embodiment of the present invention. FIG. 6 is a sectional view of a cable connection structure 100A in which an imaging element 30 is connected to the cable assembly illustrated in FIG. 5. FIG. 6 is a horizontal sectional view of the cable assembly illustrated in FIG. 5.

A cable assembly 10A includes two cables 1 and a cable fixing portion 6A that fixes the cables 1. The cable fixing portion 6A is a rectangular parallelepiped and cross sections of ends of core wires 2 are exposed on an end perpendicular to the axial direction of the cables 1. First external connection electrodes 8A-1 and second external connection electrodes 8A-2 are disposed on the end face of the cable fixing portion 6A on which the cross sections of the core wires 2 are exposed. In addition, wire patterns 7A are formed so that each connects the first external connection electrode 8A-1 and the second external connection electrode 8A-2.

The first external connection electrodes 8A-1 are disposed so as to cover the cross section exposed portions of the core wires 2 and are connected to electrodes 32 on the imaging element 30 by conductive materials 33 such as solder bumps. An electronic component 34 such as a bypass capacitor is mounted on the second external connection electrodes 8A-2.

The cable assembly 10A in the second modification of the first embodiment of the present invention, as illustrated in FIG. 6, allows the imaging element 30 and the electronic component 34 to be mounted on the end face of the cable fixing portion 6A on which the core wires 2 are exposed. The cable assembly 10A in the second modification of the first embodiment can thus be reduced in size as compared with an arrangement in which a cable assembly having an end face to which an imaging element is connected and an electronic component are mounted on a substrate. In addition, the imaging element 30 and the electronic component 34 may be juxtaposed on the end face of the cable assembly 10A.

Figure 7:
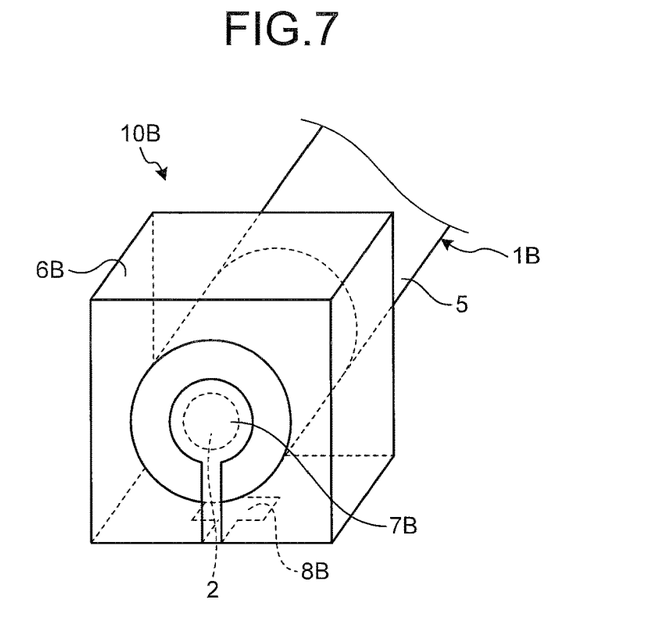
FIG. 7 is a perspective view of a mounting cable according to a third modification of the first embodiment of the present invention.

While the cable assemblies described above each include a plurality of cables fixed with the cable fixing portion, similar effects as those achieved by the foregoing arrangements can be achieved by, for example, a mounting cable in which a single cable is fixed with a cable fixing portion. FIG. 7 is a perspective view of a mounting cable according to a third modification of the first embodiment of the present invention.

This mounting cable 10B includes a cable 1B having a distal end portion fixed with a cable fixing portion 6B. The cable 1B is a metal cable that includes a jacket 5 formed of an insulator and covering an outer periphery of a core wire 2. The cable fixing portion 6B has an end face perpendicular to the axial direction of the cable 1B, on which cross sections of ends of the core wire 2 and the jacket 5 are exposed. The cable fixing portion 6B has a surface extending in parallel with the axial direction of the cable 1B, on which an external connection electrode 8B is formed and on which a wire pattern 7B is formed to extend from the core wire 2 of the cable 1B exposed on the end face to the external connection electrode 8B. The third modification of the first embodiment, too, allows the cable 1B to be connected to, for example, a substrate without the need to be folded, and thus prevents an open circuit or a short circuit. When a resin other than a fluorine-based resin is used for the jacket 5 as in the third modification, the distal end portion of the cable 1B may be covered directly in the cable fixing portion 6B without the jacket 5 peeling off from the distal end portion. Even when the jacket 5 is formed of the fluorine-based resin, giving resin adhesion to the jacket 5 to process the surface thereof through chemical treatment achieves the structure as in the third modification.

Second Embodiment

Figure 8:
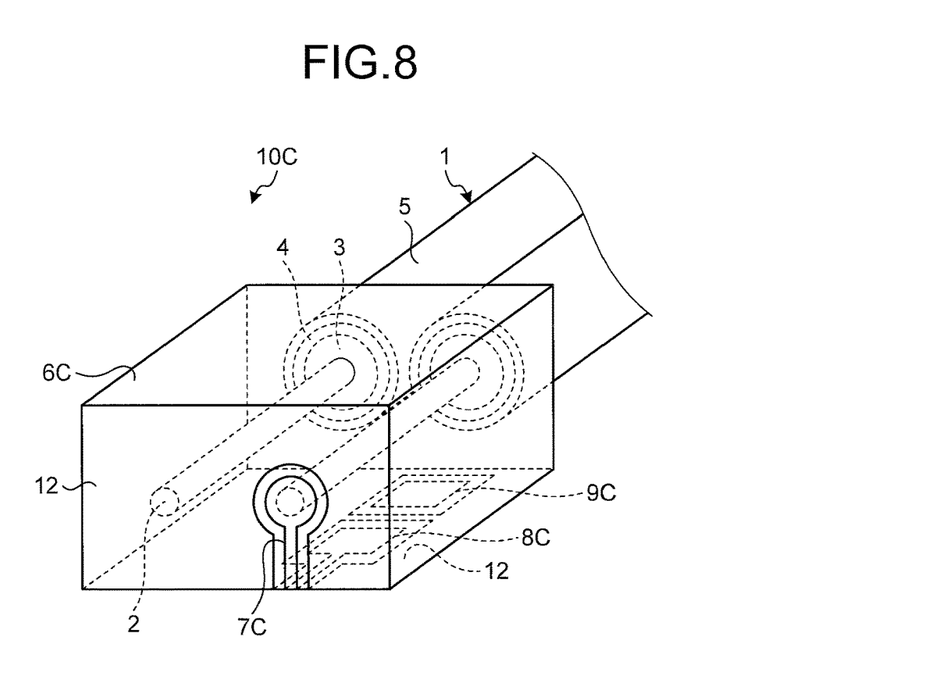
FIG. 8 is a perspective view of a cable assembly according to a second embodiment of the present invention.
Figure 9:
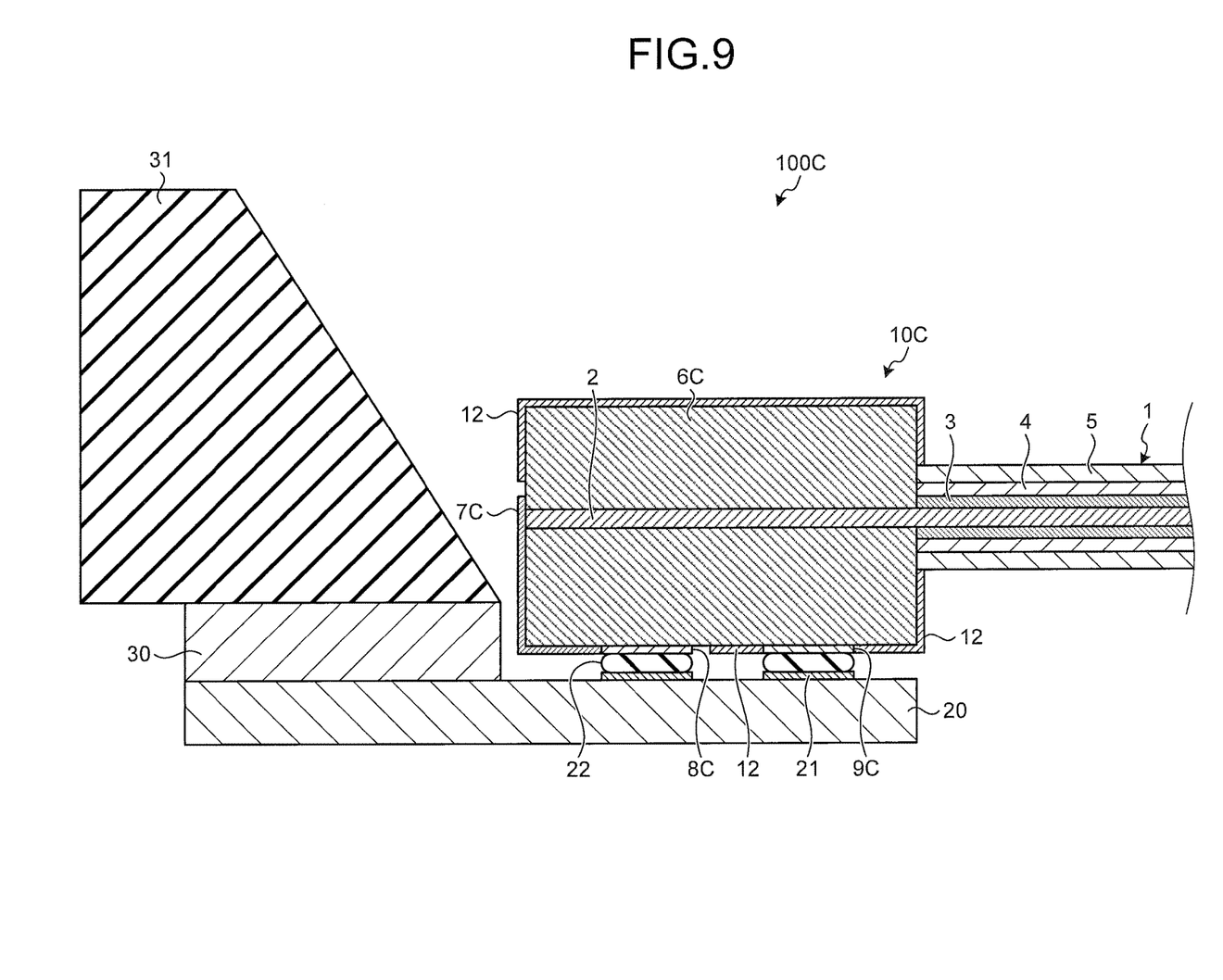
FIG. 9 is a sectional view of a cable connection structure in which the cable assembly illustrated in FIG. 8 is connected to a substrate.

In a second embodiment, a ground pattern is formed on the surface of the cable fixing portion so as to surround the wire pattern and the external connection electrode formed on the cable fixing portion. FIG. 8 is a perspective view of a cable assembly according to the second embodiment of the present invention. FIG. 9 is a sectional view of a cable connection structure 100C in which the cable assembly illustrated in FIG. 8 is connected to a substrate.

As illustrated in FIGS. 8 and 9, this cable assembly 100 according to the second embodiment includes a ground pattern 12 formed on a general surface of a cable fixing portion 6C so as to surround a wire pattern 7C, an external connection electrode 8C, and a dummy electrode 9C.

In the cable assembly 100, a core wire 2 of a cable 1 is exposed inside the cable fixing portion 6C and is susceptible to disturbance. Transmission quality can, however, be improved by forming the ground pattern 12 on the entire surface of the cable fixing portion 6C to thereby electrically shield the core wire 2.

It is noted that, when part of the core wire 2 is exposed at the distal end portion of the cable 1 inside the cable fixing portion 6C, an inner insulator 3 and a shield 4 may be exposed in a stepwise fashion and the ground pattern may be formed only on the surface of the cable fixing portion 6C around the core wire 2 that is not electrically shielded by the shield 4.

Alternatively, the ground pattern 12 may be connected to an end face of the core wire 2 that is exposed on the end face of the cable fixing portion 6C perpendicular to the axial direction of the cable 1 for grounding disposed on the left-hand side in FIG. 8. The connection between the ground pattern 12 and the end face of the core wire 2 achieves a more favorable shielding effect.

Figure 10:
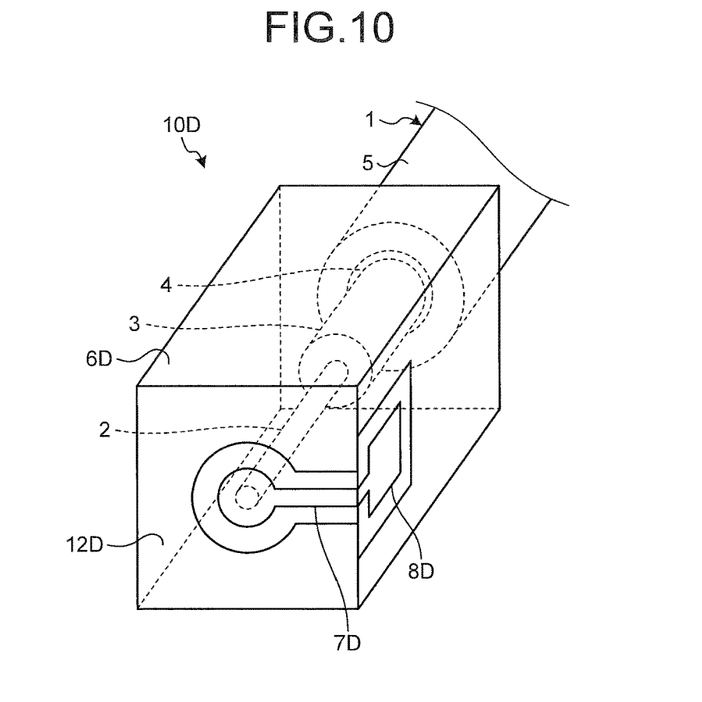
FIG. 10 is a perspective view of a mounting cable according to a first modification of the second embodiment of the present invention.

The second embodiment has been described for the cable assembly in which a plurality of cables are fixed with the cable fixing portion. Similar effects as those achieved by the foregoing arrangement can even be achieved by, for example, a mounting cable in which a single cable is fixed with a cable fixing portion. FIG. 10 is a perspective view of a mounting cable according to a first modification of the second embodiment of the present invention.

In this mounting cable 10D according to the first modification of the second embodiment, a core wire 2, an inner insulator 3, and a shield 4 are exposed in a stepwise fashion at a distal end portion of a cable 1 and a cable fixing portion 6D fixes the core wire 2, the inner insulator 3, and the shield 4 that are exposed in the stepwise fashion. A ground pattern 12D is formed on a general surface of the cable fixing portion 6D so as to surround a wire pattern 7D and an external connection electrode 8D. The formation of ground pattern 12D as described above can enhance transmission quality. In addition, when a connection is made to, for example, a substrate so that the axial direction of the cable 1 extends in parallel with the substrate, the connection can be made without the need to fold the core wire 2, which prevents an open circuit.

Third Embodiment

Figure 11:
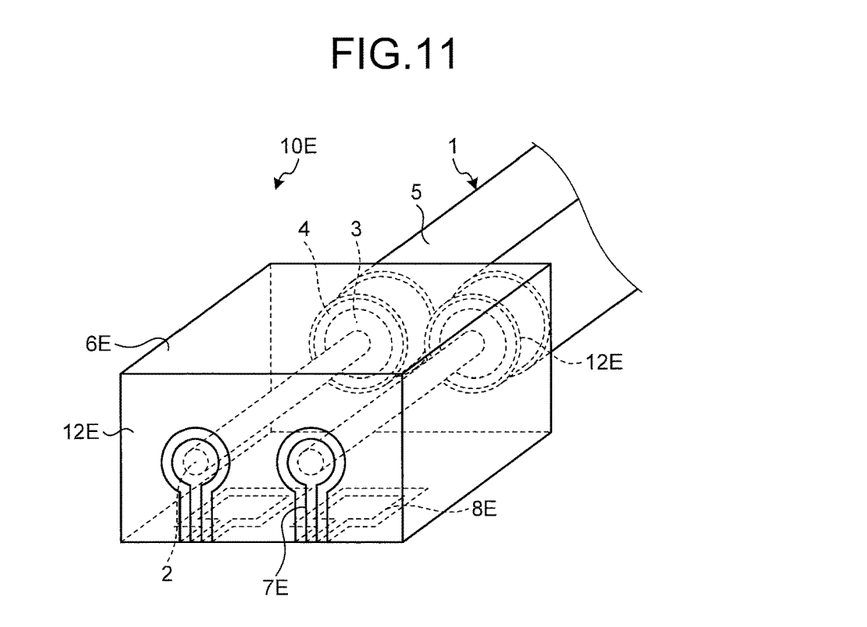
FIG. 11 is a perspective view of a cable assembly according to a third embodiment of the present invention.
Figure 12:
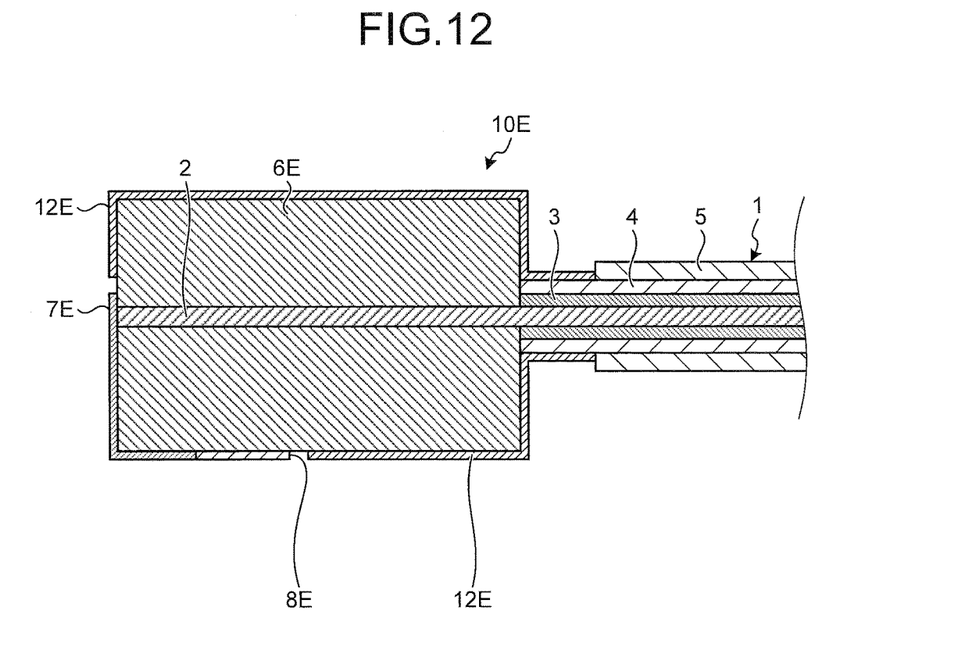
FIG. 12 is a sectional view of the cable assembly illustrated in FIG. 11.

In a third embodiment, part of the jacket of the cable near the cable fixing portion peels off to thereby expose the shield for connection to the ground pattern. FIG. 11 is a perspective view of a cable assembly according to the third embodiment of the present invention. FIG. 12 is a sectional view of the cable assembly illustrated in FIG. 11.

As illustrated in FIGS. 11 and 12, in this cable assembly 10E according to the third embodiment, a jacket 5 peels off from a portion of a cable 1 near a cable fixing portion 6E, specifically, the portion of the cable 1 not fixed with the cable fixing portion 6E, to thereby expose a shield 4. A ground pattern 12E is formed to cover an area on this exposed shield 4, so that the exposed shield 4 and the ground pattern 12E are electrically connected. Forming the ground pattern 12E to cover the area on the exposed shield 4 to electrically connect the shield 4 to the ground pattern 12E provides a further shielding effect.

To manufacture the cable assembly 10E, for example, ends of the cables 1 are fixed in the cable fixing portion 6E, end faces on which the core wires 2 are exposed are ground, the jackets 5 peel off from the cables 1 on sides adjacent to the cable fixing portion 6E to thereby expose the shields 4, the ground pattern 12E is formed on the entire surface of the cable fixing portion 6E by, for example, plating, and then wire patterns 7E and the like by, for example, etching.

Figure 13:
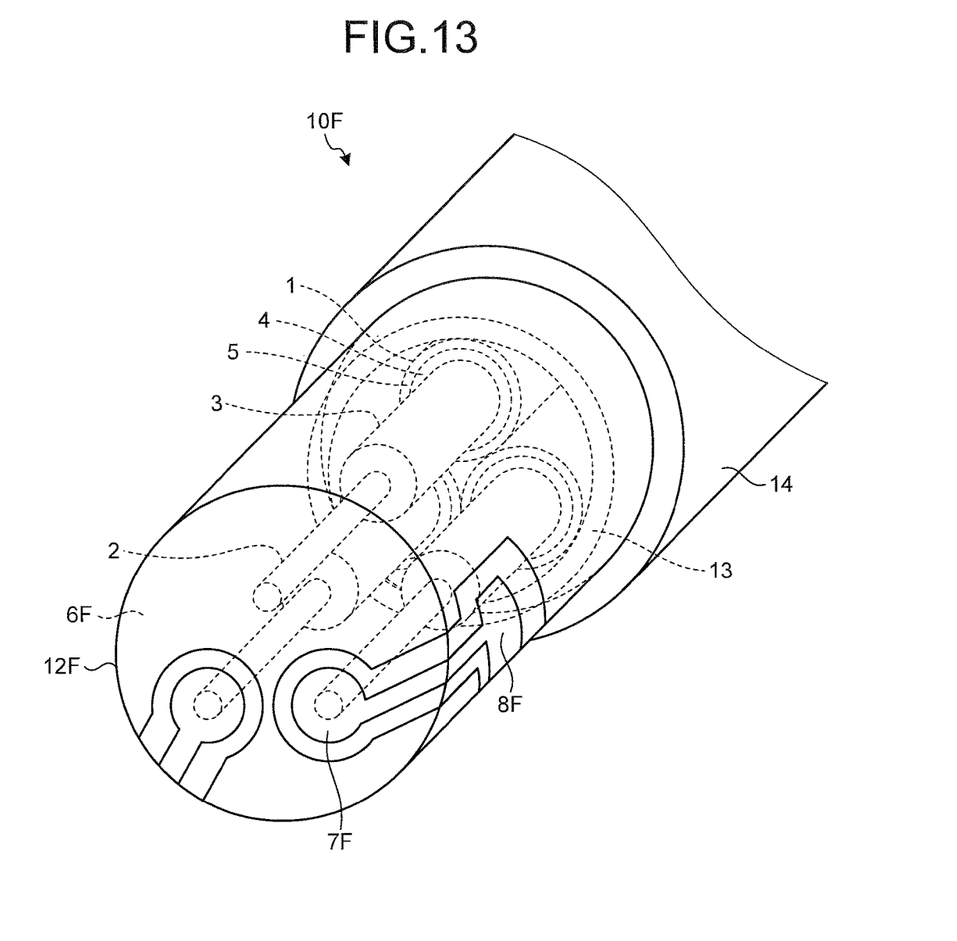
FIG. 13 is a perspective view of a cable assembly according to a first modification of the third embodiment of the present invention.
Figure 14:
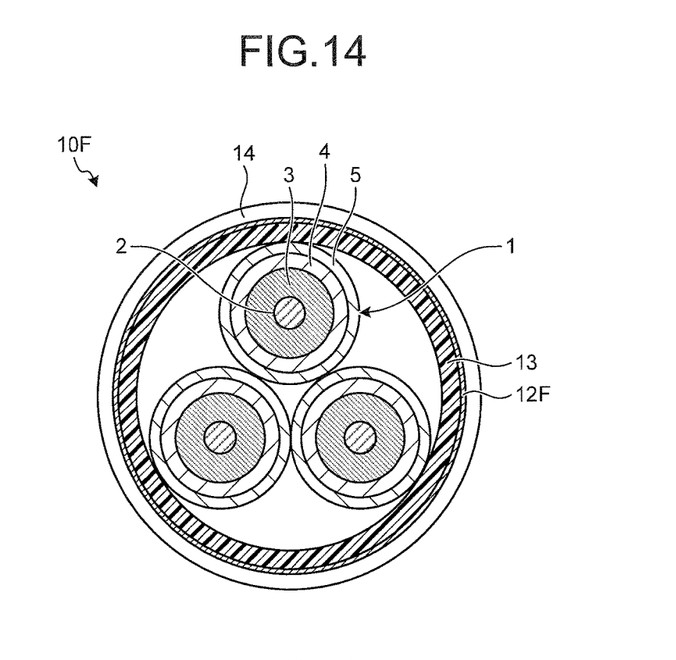
FIG. 14 is a sectional view of the cable assembly illustrated in FIG. 13.

The cable assembly may include a plurality of cables covered in an outer jacket that includes a shield assembly. FIG. 13 is a perspective view of a cable assembly according to a first modification of the third embodiment of the present invention. FIG. 14 is a sectional view of the cable assembly illustrated in FIG. 13.

In this cable assembly 10F according to the first modification of the third embodiment, each of three cables is a coaxial cable covered in an outer jacket 14 that includes a shield assembly 13. The outer jacket 14 covers the cables up to their proximal end sides. The outer jacket 14 and the shield assembly 13 peel off from distal end portions of the cables. A cable fixing portion 6F fixes a core wire 2, an inner insulator 3, and a shield 4 that are exposed in a stepwise fashion.

A ground pattern 12F is formed on a general surface of the cable fixing portion 6F so as to surround a wire pattern 7F and an external connection electrode 8F. In addition, the outer jacket 14 peels off from the side of the cable fixing portion 6F to thereby expose the shield assembly 13. The exposed shield assembly 13 is electrically connected to the ground pattern 12F. In the first modification of the third embodiment, too, forming the ground pattern 12F to cover the area on the exposed shield assembly 13 to connect the exposed shield assembly 13 electrically to the ground pattern 12F provides a further shielding effect.

Figure 15:
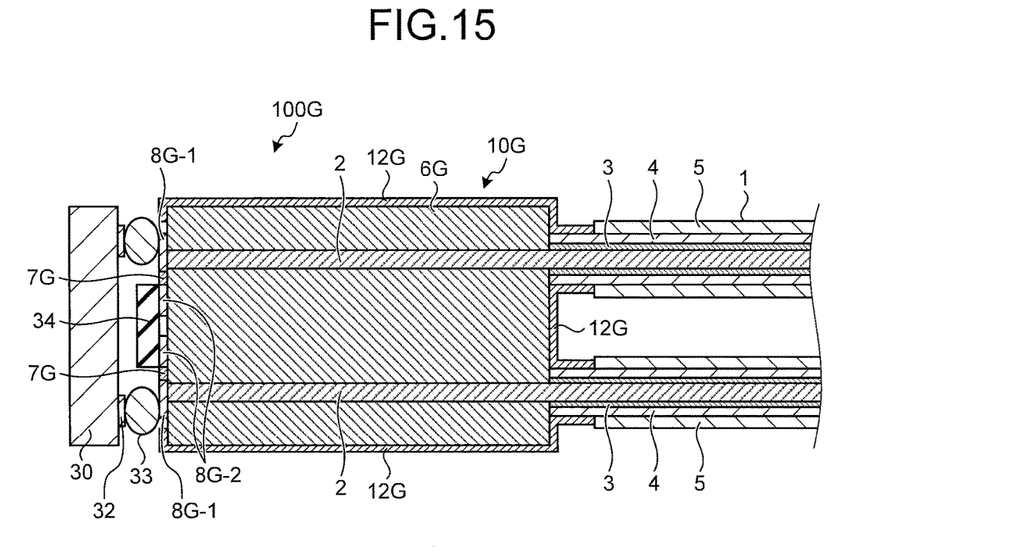
FIG. 15 is a sectional view of a cable connection structure according to a second modification of the third embodiment of the present invention.

In addition, the cable assembly having the ground pattern may have a wire pattern or the like formed on the surface of the cable fixing portion on which the core wire is exposed. FIG. 15 is a sectional view of a cable connection structure 100G according to a second modification of the third embodiment of the present invention.

A cable assembly 10G includes two cables 1 and a cable fixing portion 6G that fixes the cables 1. The cable fixing portion 6G is a rectangular parallelepiped. Cross sections of ends of core wires 2 are exposed on an end face of the cable fixing portion 6G perpendicular to the axial direction of the cables 1. First external connection electrodes 8G-1 and second external connection electrodes 8G-2 are formed on the end face of the cable fixing portion 6G on which the cross sections of the core wires 2 are exposed. Wire patterns 7G are formed to connect between the first external connection electrodes 8G-1 and the second external connection electrodes 8G-2.

The first external connection electrodes 8G-1 are formed so as to cover the cross section exposed portions of the core wires 2. The first external connection electrodes 8G-1 are connected to electrodes 32 of an imaging element 30 by conductive materials 33 such as solder bumps. An electronic component 34 such as a bypass capacitor is mounted on the second external connection electrodes 8G-2.

A ground pattern 12G is formed on a general surface of the cable fixing portion 6G so as to surround the wire patterns 7G, the first external connection electrodes 8G-1, and the second external connection electrodes 8G-2. Jackets 5 peel off from the cables 1 on the side adjacent to the cable fixing portion 6G to thereby expose shields 4. The ground pattern 12G is formed to cover areas on the exposed shields 4 and the exposed shields 4 and the ground pattern 12G are electrically connected. In the second modification of the third embodiment, too, forming the ground pattern 12G to cover the areas on the exposed shields provides a further shielding effect.

In addition, the cable assembly 10G according to the second modification of the third embodiment allows the imaging element 30 and the electronic component 34 to be mounted on the end face of the cable fixing portion 6G on which the core wires 2 are exposed. The cable assembly 10G in the second modification of the third embodiment can thus be reduced in size as compared with an arrangement in which a cable assembly having an end face to which an imaging element is connected and the electronic component 34 are juxtaposed on a substrate.

Fourth Embodiment

Figure 16:
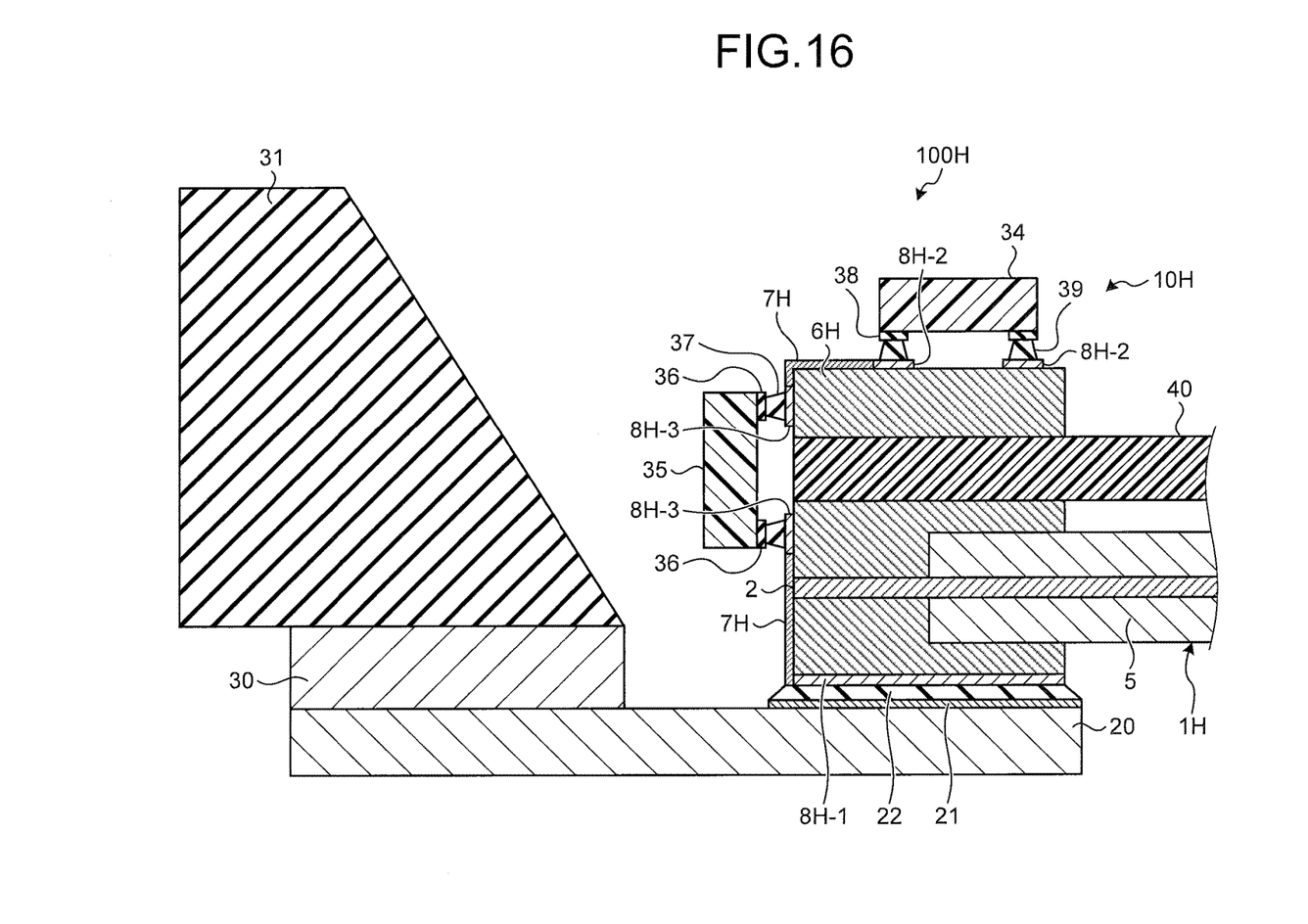
FIG. 16 is a sectional view of a cable connection structure in which a cable assembly according to a fourth embodiment of the present invention is connected to a substrate.

A cable assembly according to a fourth embodiment includes one metal cable and one optical cable. FIG. 16 is a sectional view of a cable connection structure in which the cable assembly according to the fourth embodiment of the present invention is connected to a substrate. This cable connection structure 100H illustrated in FIG. 16 is applied to an imaging module. The cable connection structure 100H includes a cable assembly 10H, a substrate 20, an imaging element 30, and a prism 31.

The cable assembly 10H includes a cable fixing portion 6H that fixes therein a cable 1H as a metal cable and an optical cable 40. The optical cable 40 includes optical fiber covered in a jacket formed of a resin or the like. The optical fiber transmits optical signals from a surface emission laser 35. The optical fiber includes a core that transmits light and a cladding disposed on an outer periphery of the core. The optical cable 40 is fixed with the cable fixing portion 6H either in a condition of being covered in a jacket or with the jacket removed. A cross section of an end of the optical cable 40 is exposed on an end face of the cable fixing portion 6H perpendicular to the axial direction of the cable 1H.

The cable 1H is a metal cable that includes a core wire 2 covered in a jacket 5 formed of an insulator. The cable 1H has a distal end portion from which the jacket 5 is removed to thereby expose the core wire 2. A cross section of an end of the core wire 2 is exposed on an end face of the cable fixing portion 6H in the axial direction of the cable 1H.

The cable fixing portion 6H is a rectangular parallelepiped. A first external connection electrode 8H-1 is formed on a side surface of the cable fixing portion 6H extending in parallel with the axial direction of the cable 1H, specifically, a bottom surface of the cable fixing portion 6H. A second external connection electrode 8H-2 is formed on an upper surface of the cable fixing portion 6H opposed to the bottom surface. In addition, a third external connection electrode 8H-3 is formed on an end face of the cable fixing portion 6H on which cross sections of the core wire 2 and the optical cable 40 are exposed. A wire pattern 7H is formed to extend from an area on the core wire 2 exposed on the end face to the first external connection electrode 8H-1, the second external connection electrode 8H-2, and the third external connection electrode 8H-3.

The cable assembly 10H is connected to an electrode 21 on the substrate 20 through a conductive material 22 via the first external connection electrode 8H-1 formed on the bottom surface of the cable fixing portion 6H.

The second external connection electrode 8H-2 is formed on the upper surface of the cable fixing portion 6H. An electronic component 34 is connected to the second external connection electrode 8H-2 through conductive materials 39.

The third external connection electrode 8H-3 is formed so as to extend across the optical cable 40 exposed on the end face of the cable fixing portion 6H. Electrodes 36 of the surface emission laser 35 are connected to the third external connection electrode 8H-3 through conductive materials 37.

The surface emission laser 35 has the center of a light-emitting region disposed coaxially with the center of a core of the optical cable 40.

The cable assembly 10H according to the fourth embodiment, including the optical cable 40, can be employed in high-speed optical communications. Connecting the cable assembly 10H so that the cable 1H and the optical cable 40 axially extend in parallel with the substrate 20 does not require that the cable 1H be folded. No space is thus required above the substrate 20 for folding the cable 1H. In addition, not requiring the core wire 2 to be folded prevents the core wire 2 from being open-circuited. Furthermore, the second external connection electrode 8H-2 and the third external connection electrode 8H-3 are disposed on side surfaces of the cable fixing portion 6H and the surface emission laser 35 and the electronic component 34 are mounted on the cable fixing portion 6H. These arrangements enable reduction in size of the cable connection structure 100H.

The second external connection electrode 8H-2, while being formed on the upper surface of the cable fixing portion 6H in the fourth embodiment, may be formed on the end face on which the surface emission laser 35 is mounted. The fourth embodiment has been exemplified by the imaging element having the surface emission laser 35 mounted on the end face of the optical cable 40. The cable assembly according to the fourth embodiment is not, however, limited to the foregoing arrangement and may include a light-receiving element, such as a photodiode, mounted thereon.

Note 1. A cable assembly including: a plurality of cables; and a cable fixing portion that fixes end portions of the plurality of cables, wherein at least one of the plurality of cables is a metal cable that includes a core wire formed of a conductive material and a jacket formed of an insulator and covering the core wire; the jacket is removed from a portion of the metal cable inside the cable fixing portion; and the cable fixing portion has an end face which is perpendicular to an axial direction of the plurality of cables and on which cross sections of end portions of core wires of the plurality of cables are exposed, and the cable assembly further includes: first and second external connection electrodes on the end face of the cable fixing portion so as to cover the exposed cross sections of the core wires: a wire pattern formed between the first and second external connection electrodes; and a ground pattern formed on a surface of the cable fixing portion so as to surround the wire pattern, and the first and second external connection electrodes.

Note 2. A cable connection structure including a cable assembly and an imaging element connected to the cable assembly, the cable assembly including: a plurality of cables each having a core wire and a jacket formed of an insulator and coving the core wire; and a cable fixing portion that fixes the plurality of cables, wherein the cable fixing portion has an end face which is perpendicular to an axial direction of the plurality of cables and on which cross sections of end portions of core wires of the plurality of cables are exposed, and the cable connection structure further includes: a first external connection electrode for the imaging element and a second external connection electrode for connecting to an electronic component, the first and second connection electrodes being formed on the end face so as to cover the cross sections of the core wires; and a wire pattern formed between the first and second external connection electrodes.

Note 3. The cable connection structure according to Note 2, further including a ground pattern formed on a surface of the cable fixing portion so as to surround the wire pattern, and the first and second external connection electrodes.

Note 4. A cable connection structure including a cable assembly and a mounting member connected to the cable assembly, the cable assembly including: a plurality of cables each having a core wire and a jacket formed of an insulator and coving the core wire; and a cable fixing portion that fixes the plurality of cables, wherein the cable fixing portion has an end face which is perpendicular to an axial direction of the plurality of cables and on which cross sections of end portions of core wires of the plurality of cables are exposed, and the cable connection structure further includes: an external connection electrode formed on at least one surface of the cable fixing portion, the at least one surface being in parallel with the axial direction of the plurality of cables; and wire pattern that extends from an area on the core wires exposed on the end face to the external connection electrode to thereby connect to the mounting member through the external connection electrode.

In accordance with some embodiments, the cable end is fixed with the cable fixing portion and the external connection electrode to be connected to, for example, a substrate or an electronic component is formed on the surface of the cable fixing portion extending in parallel with the cable axial direction. The cable can thus be connected to the mounting surface of the substrate in parallel therewith without the need to be folded. In addition, the electronic component can be mounted on the surface of the cable fixing portion. Thus, flexibility in designing the connection structure can be enhanced and the connection structure can be reduced in size.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

REFERENCE SIGNS LIST

1 CABLE
2 CORE WIRE
3 INNER INSULATOR
4 SHIELD
5 JACKET
6 CABLE FIXING PORTION
7 WIRE PATTERN
8, 8B, 8C, 8D, 8E, 8F EXTERNAL CONNECTION ELECTRODE
9 DUMMY ELECTRODE
10 CABLE ASSEMBLY
12 GROUND PATTERN
13 SHIELD ASSEMBLY
14 OUTER JACKET
20 SUBSTRATE
21 ELECTRODE
22 CONDUCTIVE MATERIAL
30 IMAGING ELEMENT
31 PRISM
34 ELECTRONIC COMPONENT
36, 38 ELECTRODE

What is claimed is:

1. A mounting cable comprising:
   a metal cable that includes a core wire formed of a conductive material and a jacket formed of an insulator and covering the core wire, a part of the jacket being removed to form an exposed portion of the core wire;
   a cable fixing portion that accommodates at least the exposed portion of the core wire, the cable fixing portion having an end face which is a planar exterior surface, the end face being perpendicular to an axial direction of the metal cable and on which a cross section of the exposed portion of the core wire is exposed, the cable fixing portion having an insulation property;
   an external connection electrode formed on one exterior surface of the cable fixing portion, the one exterior surface being a planar surface perpendicular to the end face, the external connection electrode having a connection surface that is an exterior and exposed planar surface in parallel with the axial direction of the metal cable; and
   a wire pattern that is formed on a surface of the cable fixing portion and extends from the cross-section of the exposed portion of the core wire to the external connection electrode;
   an optical cable formed on a second exterior surface of the cable fixing portion;
   a surface emission laser formed on the end face and in electrical connection with the core wire;
   wherein the optical cable is configured to transmit optical signals from the surface emission laser.

2. The mounting cable according to claim 1, wherein
   the metal cable is a coaxial cable that includes the core wire formed of the conductive material, an inner insulator which covers an outer periphery of the core wire, a shield which covers an outer periphery of the inner insulator, and the jacket which covers an outer periphery of the shield with the insulator,
   the coaxial cable in the cable fixing portion has a distal end portion on which the core wire is exposed, and
   the mounting cable further comprises a ground pattern formed on a surface of the cable fixing portion so as to surround the wire pattern and the external connection electrode.

3. The mounting cable according to claim 2, wherein
   in the coaxial cable, part of the jacket near the cable fixing portion peels off to expose the shield, and
   the ground pattern is formed so as to cover the exposed shield.

4. The mounting cable according to claim 1, wherein the cable fixing portion is formed of a curable resin.

5. The mounting cable according to claim 1, further comprising an electronic component mounted on the cable fixing portion.

6. A cable assembly comprising:
   a plurality of cables, each of the plurality of cables having a metal cable that includes a core wire formed of a conductive material and a jacket formed of an insulator and covering the core wire, a part of the jacket being removed from each of the plurality of cables to form an exposed portion of the core wire;
   a cable fixing portion that accommodates at least the exposed portion of the core wire of each of the plurality of cables, the cable fixing portion having an end face which is a planar exterior surface, the end face being perpendicular to an axial direction of the plurality of cables and on which a cross section of the exposed portion of the core wire of each of plurality of cables are exposed, the cable fixing portion having an insulation property;
   an external connection electrode formed on one exterior surface of the cable fixing portion, the one exterior surface being a planar surface perpendicular to the end face, the external connection electrode having at least one connection surface that is an exterior and exposed planar surface in parallel with the axial direction of the plurality of cables; and
   a wire pattern that is formed on a surface of the cable fixing portion and extends from the cross-section of the core wire of each of the plurality of cables to the at least one external connection electrode;
   an optical cable formed on a second exterior surface of the cable fixing portion;
   a surface emission laser formed on the end face and in electrical connection with the core wire;
   wherein the optical cable is configured to transmit optical signals from the surface emission laser.

7. The cable assembly according to claim 6, wherein
each of the plurality of cables is a coaxial cable that includes the core wire formed of the conductive material, an inner insulator which covers an outer periphery of the core wire, a shield which covers an outer periphery of the inner insulator, and the jacket which covers an outer periphery of the shield with the insulator, the coaxial cable in the cable fixing portion has a distal end portion on which the core wire is exposed, and the cable assembly further comprises a ground pattern formed on a surface of the cable fixing portion so as to surround the wire pattern and the at least external connection electrode.

8. The cable assembly according to claim 7, wherein
in the coaxial cable, part of the jacket near the cable fixing portion peels off to expose the shield, and the ground pattern on the surface of the cable fixing portion is formed so as to cover the exposed shield.

9. The cable assembly according to claim 6, wherein
one of the plurality of cables is an optical cable, and the optical cable has a cross section of an end portion exposed on the end face of the cable fixing portion.

10. The cable assembly according to claim 6, wherein
the plurality of cables are disposed three-dimensionally and fixed with the cable fixing portion, and as many external connection electrodes as the plurality of cables are formed on one surface of the cable fixing portion, the one surface being in parallel with the axial direction of the plurality of cables.

11. The cable assembly according to claim 6, wherein the cable fixing portion is formed of a curable resin.

12. The cable assembly according to claim 6, further comprising an electronic component mounted on the cable fixing portion.

* * * * *